United States Patent [19]

Hirano et al.

[11] Patent Number: 4,520,162

[45] Date of Patent: May 28, 1985

[54] POLYMERIC COMPOUNDS WITH SUSTAINED ANTI-TUMOR ACTIVITY AND A METHOD FOR THE PREPARATION THEREOF

[75] Inventors: Takashi Hirano; Shinichi Ohashi, both of Sakura; Satoshi Morimoto, Yatabe; Masaru Shiraki; Keishiro Tsuda, both of Sakura; Tomowo Kobayashi; Shigeru Tsukagoshi, both of Tokyo, all of Japan

[73] Assignee: Director-General of the Agency of Industrial Science & Technology, Tokyo, Japan

[21] Appl. No.: 651,343

[22] Filed: Sep. 17, 1984

[30] Foreign Application Priority Data

Sep. 24, 1983 [JP] Japan ................................. 58-176833
Sep. 24, 1983 [JP] Japan ................................. 58-176834

[51] Int. Cl.$^3$ .............................................. C08F 8/32
[52] U.S. Cl. ................................ 525/327.6; 525/366; 525/375; 525/380
[58] Field of Search ..................... 525/327.6, 366, 325, 525/380

[56] References Cited

U.S. PATENT DOCUMENTS

| | | | |
|---|---|---|---|
| 3,941,756 | 3/1976 | Hoper et al. | 525/327.6 |
| 4,182,800 | 1/1980 | Ringsdorf et al. | 525/375 |
| 4,309,413 | 1/1982 | Fields et al. | 525/327.6 |
| 4,366,294 | 12/1982 | Williams et al. | 525/327.6 |

Primary Examiner—Bernard Lipman
Attorney, Agent, or Firm—Brisebois & Kruger

[57] ABSTRACT

The novel polymeric compound proposed in the invention has a backbone structure formed of a copolymeric moiety of maleic anhydride and divinyl ether and pendant groups thereon derived from an anthracycline-type anti-tumor agent, e.g. adriamycin and daunomycin, or 1-$\beta$-D-arabinofuranosylcytosine bonded to the maleic anhydride units in the backbone structure by forming amide linkages, the remaining anhydride units in the backbone structure being hydrolyzed into free acid form or a salt thereof. Both in vitro and in vivo tests indicate that the anti-tumor active pendant groups in the polymeric compound can be released sustainedly to exhibit the anti-tumor activity with greatly decreased side effects unavoidable when the above mentioned anti-tumor agents as such are administered to a patient in a relatively large dose.

5 Claims, 6 Drawing Figures

POLYMERIC COMPOUNDS WITH SUSTAINED ANTI-TUMOR ACTIVITY AND A METHOD FOR THE PREPARATION THEREOF

BACKGROUND OF THE INVENTION

The present invention relates to a novel polymeric compound having sustained anti-tumor activity and a method for the preparation thereof. More particularly, the invention relates to a polymeric compound with a polymeric backbone structure and pendant groups thereon having anti-tumor activity, which can be sustainedly released to exhibit the desired activity after administration.

As is known, several classes of organic compounds have anti-tumor or anti-cancer activity including, for example, nucleic acid derivatives and certain kinds of antibiotics. Among them, remarkable anti-tumor effects are obtained and clinical treatment is widely undertaken with 1-β-D-arabinofuranosylcytosine against leukemia and with 5-fluorouracil and related compounds against solid tumors as the examples of the former class and anthracycline-type antibiotics, e.g. adriamycin and daunomycin, against acute leukemia and children's cancer as the examples of the latter class.

Along with the excellent anti-tumor activity, unfortunately, these known anti-tumor agents exhibit strong toxicity also to normal cells and various undesirable side effects are unavoidable in the administration of them to patients. For example, the anthracycline-type antibiotics cause decrease in the leukocytes and blood platelets, hepatopathy and other side effects. Therefore, clinical administration of these anti-tumor agents must be performed under more than sufficient caution against possible side effects so that the anti-tumor agent is usually administrated many times in small portions of dose bit by bit in a generally accepted therapeutic practice. Such a way of administration of a medicament is of course very troublesome and it is eagerly desired to develop an anti-tumor agent which can be administrated less frequently to a patient with no apprehension of the side effects.

SUMMARY OF THE INVENTION

An object of the present invention is therefore to provide an anti-tumor agent capable of complying with the above mentioned medical and pharmacological demand and sustainedly exhibiting an anti-tumor activity when administered in a relatively large dose without the problem of side effects.

The novel polymeric compound of the invention is a polymer having a polymeric backbone structure which is a copolymeric moiety of maleic anhydride and divinyl ether (referred to as DIVEMA hereinafter) expressed by the structural formula in which n is a positive integer of at least 2, and pendant moiety thereon with an anti-tumor activity bonded to the backbone structure of the above mentioned copolymeric moiety through an amide linkage formed between the carbonyl group in the maleic anhydride unit of the backbone polymer and the amino group in the pendant moiety, the pendant moiety being specifically a 1-β-D-arabinofuranosylcytosine moiety or an anthracycline moiety, so that the inventive polymeric compound can be represented by the general formula in which n has the same meaning as defined above and R is the respective active pendant group derived from the above mentioned active moiety, with conversion of the anhydride structure into the free acid form by hydrolysis or salts thereof by neutralization. More specifically, the anthracycline moiety should be adriamycin or daunomycin having an amino group in a molecule reactive with the maleic anhydride unit in the DIVEMA.

The above described polymeric compound of the invention can readily be prepared by the reaction of the DIVEMA polymer and the respective active agent in an organic solvent such as N-methylpyrrolidone in the presence of a catalyst such as triethylamine followed by hydrolysis of the reaction product to convert the anhydride structure into free acid form which can further be converted to a salt form according to need.

DETAILED DESCRIPTION OF THE PREFERRED EMBODIMENTS

Thus, the inventors have continued extensive investigations being guided by an idea that a composite polymeric compound composed of a polymeric backbone structure and pendant groups thereon with an anti-tumor activity would be promising provided that the active pendant groups are sustainedly released after administration and the anti-tumor activity is exhibited only by the thus released pendant groups and have arrived at a discovery that the practically useful combination of the polymeric backbone structure and the pendant groups is limited to specific types of them leading to the establishment of the present invention to provide the above described novel class of polymeric compounds. When such a polymeric compound is administrated to a patient, the active moiety is sustainedly released in the human body over certain length of time to maintain a concentration level of the compound in the blood with a different distribution thereof in the body so that the toxicity of the active compound against normal cells is mitigated without reducing the anti-tumor activity thereof.

The extensive experimental works undertaken by the inventors have led to a discovery that the DIVEMA, i.e. copolymer of maleic anhydride and divinyl ether, is the most suitable for the above purpose when the active moiety in the polymer should be anthracycline-type antibiotics or 1-$\beta$-D-arabinofuranosylcytosine. As is known, DIVEMA itself has a certain degree of anti-tumor activity and, by virtue of the large number of the anhydride units in the structure, is reactive with the amino groups in the above mentioned active agents readily to form an amide linkage. Moreover, the amide linkages formed between the DIVEMA moiety and the active pendant groups are susceptible to hydrolysis under moderate conditions so that sustained release of the active moiety is expected under not only in vitro but also in vivo conditions.

The DIVEMA polymer used as the backbone moiety of the inventive polymeric compound is expressed by the general formula (I) given above and can be prepared by the copolymerization of maleic anhydride and divinyl ether according to a known procedure described in, for example, U.S. Pat. No. 3,320,216. As is mentioned above, the DIVEMA polymer itself has a certain degree of anti-tumor activity against various types of tumors. Particularly preferable of the DIVEMA polymer are those having a relatively low molecular weight of less than 100,000 or, more preferably, less than 30,000 in respect of the outstandingly low toxicity with a reported $LD_{50}$ value of 700 mg/kg body weight or larger. The anhydride structure in the DIVEMA polymer is reactive with the amino group in the anti-tumor active agent to form an amide linkage so that the polymer is very suitable as a "carrier" of the active agent.

The first class of the anti-tumor active agent to be the pendant groups on the polymeric backbone structure of the DIVEMA includes the anthracycline-type antibiotics represented by the general formula (III)

in which R' is a hydroxyl group or a methyl group to give adriamycin or daunomycin, respectively, the pendant group R in the formula (II) then being expressed by the formula (IV)

These antibiotics are also known as an excellent anti-tumor agent against acute leukemia and children's cancer and can be therapeutically useful if it were not for the relatively strong toxicity against normal cells. Having a reactive amino group in a molecule, these anthracycline-type antibiotic substances can react with the DIVEMA polymer in an organic solvent such a N-methylpyrrolidone, dimethylsulfoxide, dimethylformamide and the like in the presence of a catalyst such as a tertiary amine, e.g. triethylamine, to form an amide linkage at the acid anhydride structure and the reaction product is then hydrolyzed to convert the unreacted acid anhydride structure into a free acid form followed by purification to remove the unreacted materials or other impurities in a suitable purification procedure such as ion-exchange and ultrafiltration and then by freeze-drying into a solid form. If it is desired to impart the polymeric compound with increased solubility in water, the reaction product obtained by the hydrolysis may be converted into a pharmocologically acceptable salt form with a metal such as sodium, potassium, calcium, magnesium and the like before purification and drying. The content of the anthracycline-type antibiotic moiety in the inventive polymeric compound is preferably in the range from 5 to 40% by weight.

Another class of the anti-tumor active agent to form the pendant groups on the polymeric backbone structure of DIVEMA is 1-$\beta$-D-arabinofuranosylcytosine expressed by the structural formula (V)

the pendant group R in the formula (II) then being expressed by the formula (VI)

This compound is also known to have an excellent antitumor activity against leukemia and other types of tumors and can be therapeutically useful it it were not for the relatively strong toxicity against normal cells. Having a reactive amino group in a molecule, this compound also can react with the DIVEMA polymer followed by hydrolysis to give the inventive polymeric compound of the free acid form or a salt thereof in just the same manner as in the case of the anthracycline-type antibiotics. The preferable content of the active pendant moiety in this case is also in the range from 5 to 40% by weight.

When the inventive polymeric compound having the anti-tumor active moiety pendant on the backbone structure is administrated to a patient, the amide linkages between the backbone structure and the pendant groups are gradually decomposed by virtue of the catalytic activity of the free carboxyl groups and/or enzymatic hydrolysis to liberate the anti-tumor active agent. Thus, the polymeric compounds provided by the invention, which are novel compounds not known nor described in any prior art literatures, are promising as a sustainedly active anti-tumor agent with little problem of side effects and much better therapeutic results can be expected by the administration thereof than in the single use of the anthracycline-type anti-tumor agents or 1-β-D-arabinofuranosylcytosine alone partly owing to the synergistic effect with the DIVEMA polymer which in itself has a certain degree of anti-tumor activity. In comparison with 1-β-D-arabinofuranosylcytosine per se, in particular, which is administrated usually by instillation taking a certain length of time to cause great pain to the patient due to the relatively rapid deamination in the human body, the inventive polymeric compound having this anti-tumor agent as the pendant groups can be administrated by an ordinary injection by virtue of the stability against deamination.

For example, an in vitro test indicated that the inventive polymeric compound having adriamycin as the pendant groups released about 20% of the combined adriamycin in two weeks in a 0.1N phosphate buffer solution of pH 7.2. Further, an animal test using a group of mice implanted with P388 leukemia cells indicated that the inventive polymeric compound having daunomycin as the pendant groups on the DIVEMA polymer had an anti-tumor activity to give a maximum life prolongation of 98% while the corresponding value with daunomycin as such was 48% in the comparative test undertaken concurrently.

EXAMPLE 1

A polymeric compound having adriamycin as the pendant groups on the DIVEMA polymer was prepared in the following manner. Thus, 90 mg of DIVEMA polymer having an average molecular weight of about 28,500 and a value of $M_w/M_n$ of 1.89 were dissolved in 1 ml of anhydrous N-methylpyrrolidone and 5 ml of an N-methylpyrrolidone solution containing 90 mg of adriamycin hydrochloride were added dropwise to the solution under agitation and then 5 ml of an N-methylpyrrolidone solution containing 50 µl of anhydrous triethylamine as the catalyst were added dropwise thereto over a period of 10 minutes to effect the reaction between the reactants. The reaction was performed at room temperature for 12 hours in dark.

After completion of the reaction, the reaction mixture was added dropwise into 1 liter of n-hexane under vigorous agitation so that a red solid precipitated in the solution, which was collected by filtration and washed with 1 liter of fresh n-hexane. The solid material was dispersed in 5 ml of re-distilled water and the pH of the dispersion was adjusted to 7.0 by adding a 1% by weight aqueous solution of sodium hydrogencarbonate with agitation. The solid material was completely dissolved within 1 hour to give a clear red solution. With an object to remove the unreacted adriamycin and the triethylamine used as the catalyst, ion-exchange treatment was repeated twice each time by adding 200 mg of a strongly acidic cation exchange resin (Dowex 50W-X4, a product by Dow Chemical Co.) to the solution followed by filtration after 10 minutes of agitation and washing of the resin on the filter paper with 10 ml of water. The solution was subjected to ultrafiltration using an ultrafiltration membrane (Diaflow Membrane PM10, a product by Amicon Co.) corresponding to fractionation of a critical molecular weight of 10,000 followed by washing with re-distilled water. When the filtrate solution became completely colorless, the filtration procedure was terminated and the solution was passed through a Millipore Filter (a product by Millipore Co.) having a pore diameter of 0.22 µm followed by freeze drying to give 177 mg of a reddish orange, flue-like solid material.

Figure 1:
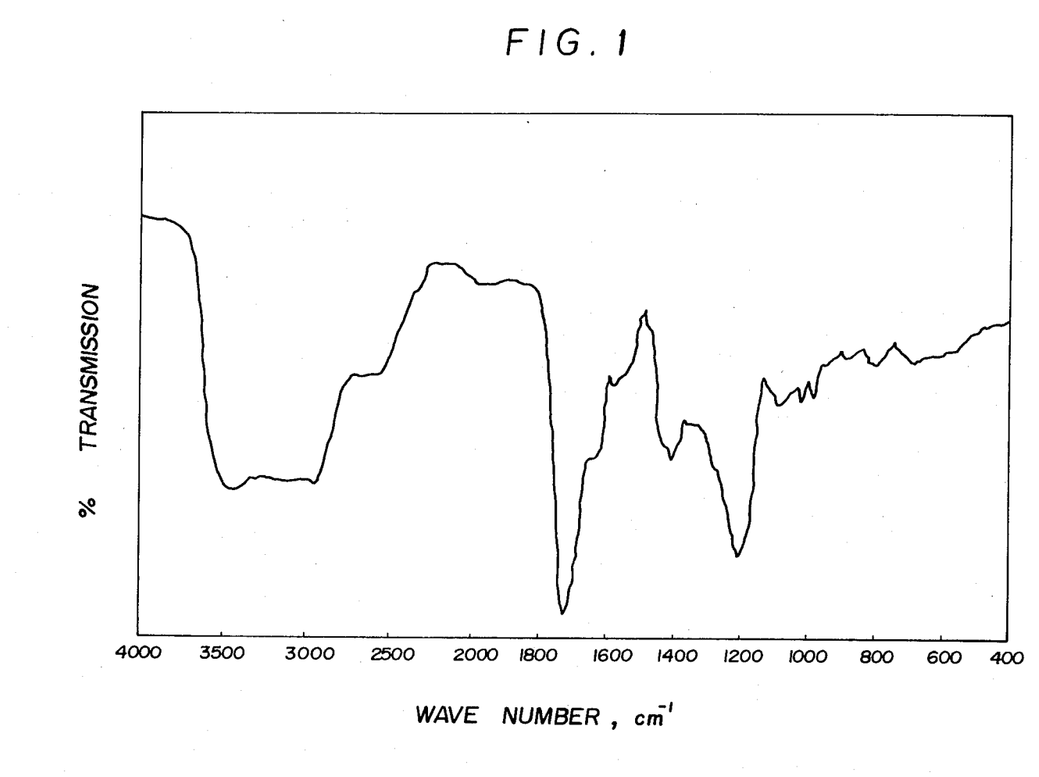
FIG. 1 illustrates an infrared absorption spectrum of the inventive polymer with the adriamycin groups pendant on the DIVEMA backbone prepared in Example 1.
Figure 2:
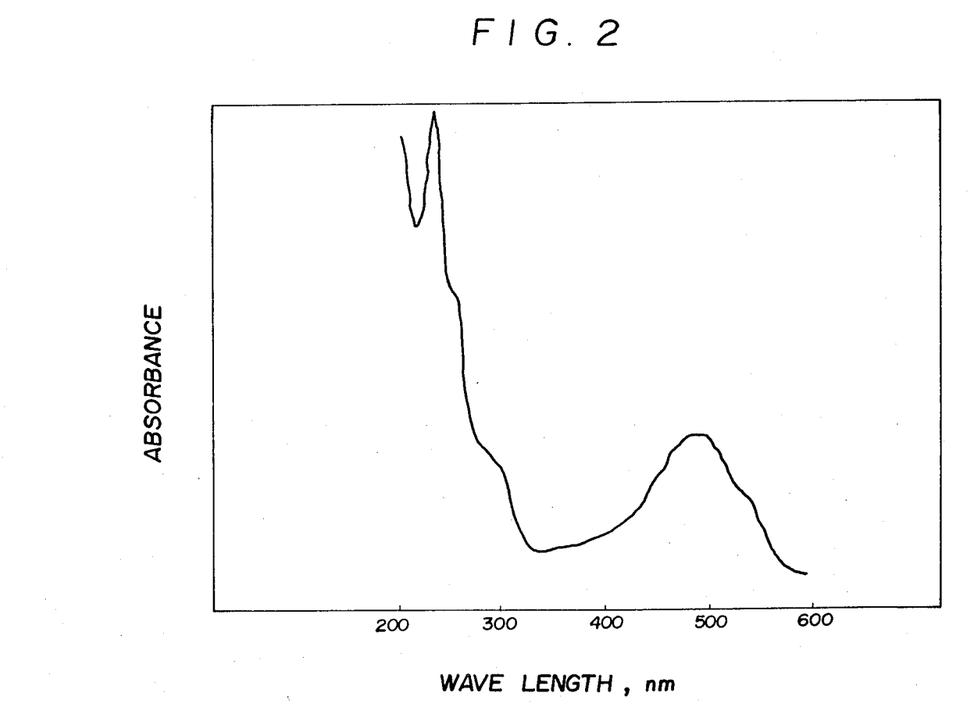
FIG. 2 illustrates a visible to ultraviolet absorption spectrum of the same polymer as in FIG. 1.

The thus obtained solid product was soluble in water and polar organic solvents such as dimethylsulfoxide, dimethylformamide, N-methylpyrrolidone and the like but insoluble in diethyl ether, n-hexane, benzene and the like. The infrared absorption sepectrum in KBr tablet and the visible to ultraviolet absorption spectrum in water of this compound are shown in FIGS. 1 and 2, respectively. According to the estimation from the absorbance at a wave length of 490 nm, the product contained 31.3% by weight of adriamycin. The absorption bands appearing in the visible to ultraviolet absorption spectrum had the maxima at 491, 292, 253 and 234 nm while the infrared absorption spectrum had absorption bands at 3450, 2930, 1720, 1670, 1630, 1610, 1580, 1530, 1440, 1410, 1380, 1280, 1250, 1200, 1110, 1070, 1010 and 980 cm$^{-1}$.

EXAMPLE 2

Figure 3:
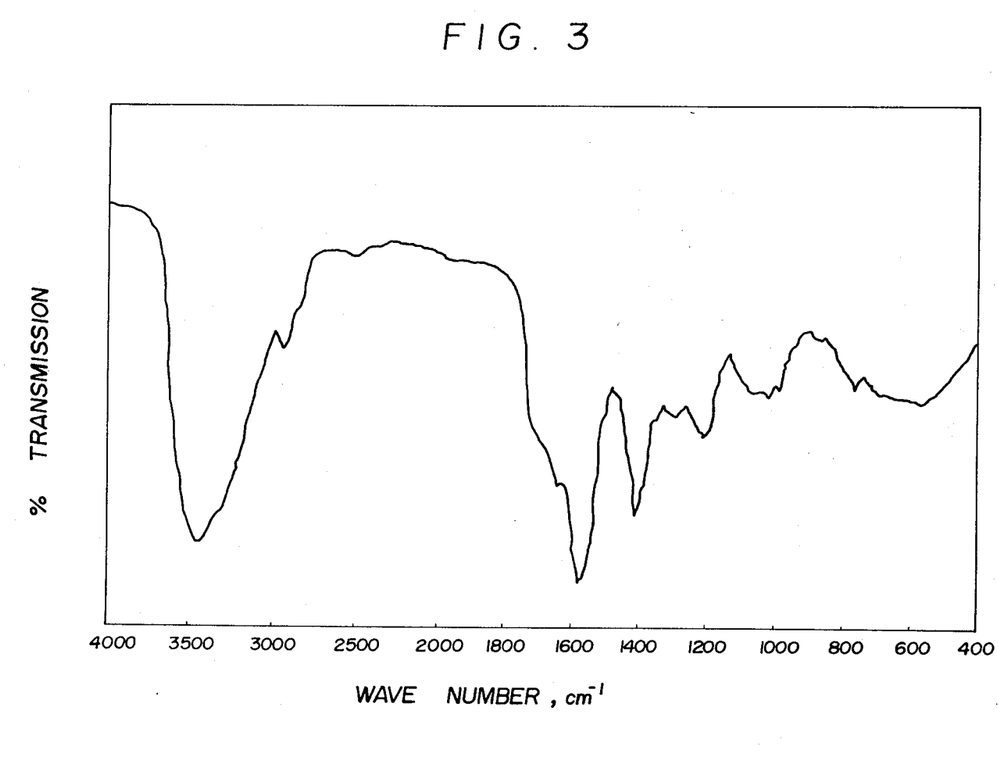
FIG. 3 illustrates an infrared absorption spectrum of a polymer similar to that of FIG. 1 but in the salt form prepared in Example 2.

The aqueous solution prepared by dissolving the adriamycin-bearing DIVEMA polymer obtained in Example 1 in water having a pH of 4.6 was admixed with a 0.1% by weight aqueous solution of sodium hydrogencarbonate to have a pH of 7.0 followed by filtration through a Millipore Filter having a pore diameter of 0.22 µm and freeze drying to give a dark red, flue-like solid material. The yield of the thus obtained sodium salt was quantitative based on the free acid form in Example 1. This product was more readily soluble in water than the product obtained in Example 1. When compared with FIG. 1, the infrared absorption spectrum of this product shown in FIG. 3 had a strong absorption at 1580 cm$^{-1}$ while the absorption at 1720 cm$^{-1}$ apparently decreased. The visible to ultraviolet absorption spectrum was substantially the same as that shown in FIG. 2.

EXAMPLE 3

Substantially the same preparation procedure as in Example 1 was repeated by the reaction of 100 mg of the same DIVEMA polymer and 15 mg of adriamycin hydrochloride in 10 ml of anhydrous N-methylpyrrolidone with 5.4 μl of triethylamine as the catalyst. A similar post-treatment of the reaction mixture to that in Example 1 gave 130 mg of a reddish orange, flue-like solid product which contained 9.4% by weight of adriamycin according to the estimation from the absorption in the visible region. The infrared absorption and visible to ultraviolet absorption spectra of this product were substantially the same as those shown in FIGS. 1 and 2, respectively.

EXAMPLE 4

In a similar manner to Example 1, 50 mg of the same DIVEMA polymer and 50 mg of daunomycin hydrochloride were reacted in 10 ml of anhydrous N-methylpyrrolidone with 10 μl of triethylamine as the catalyst followed by the same post-treatment of the reaction mixture as in Example 1 to give 104 mg of a reddish orange, flue-like solid material which contained 24.8% by weight of daunomycin according to the estimation from the absorption spectrum in the visible region.

EXAMPLE 5

The reaction product obtained in Example 4 was treated in a similar manner to Example 2 to give a dark red, flue-like solid material which was in a form of the sodium salt. The yield of this salt form product was quantitative based on the free acid form product obtained in Example 4. The infrared absorption spectrum of this product had a strong absorption appearing at 1580 cm$^{-1}$ while the absorption at 1720 cm$^{-1}$ apparently decreased. The visible to ultraviolet absorption spectrum of this product was substantially the same as that of the product in Example 4.

EXAMPLE 6

A polymeric compound of DIVEMA having 1-β-D-arabinofuranosylcytosine, referred to as AraC hereinafter, as the pendant groups was prepared from 500 mg of the same DIVEMA polymer as used in Example 1 dissolved in 40 ml of N-methylpyrrolidone with admixture of 1.50 g of AraC and 0.25 ml of triethylamine to be reacted for 24 hours at room temperature. The reaction mixture was poured into 500 ml of water and the pH value of the aqueous solution was adjusted to 8.0 by adding an aqueous solution of sodium hydrogencarbonate. After standing for 2 hours, the solution was acidified to a pH of about 3 by use of a 1N hydrochloric acid and then the pH of the solution was brought to 5.0 by adding a 1N aqueous solution of sodium hydroxide followed by filtration through the same ultrafiltration membrane as used in Example 1 to remove the unreacted reactants, organic solvent and salt and freeze drying to give 920 mg of a white powder as the desired product.

Figure 4:
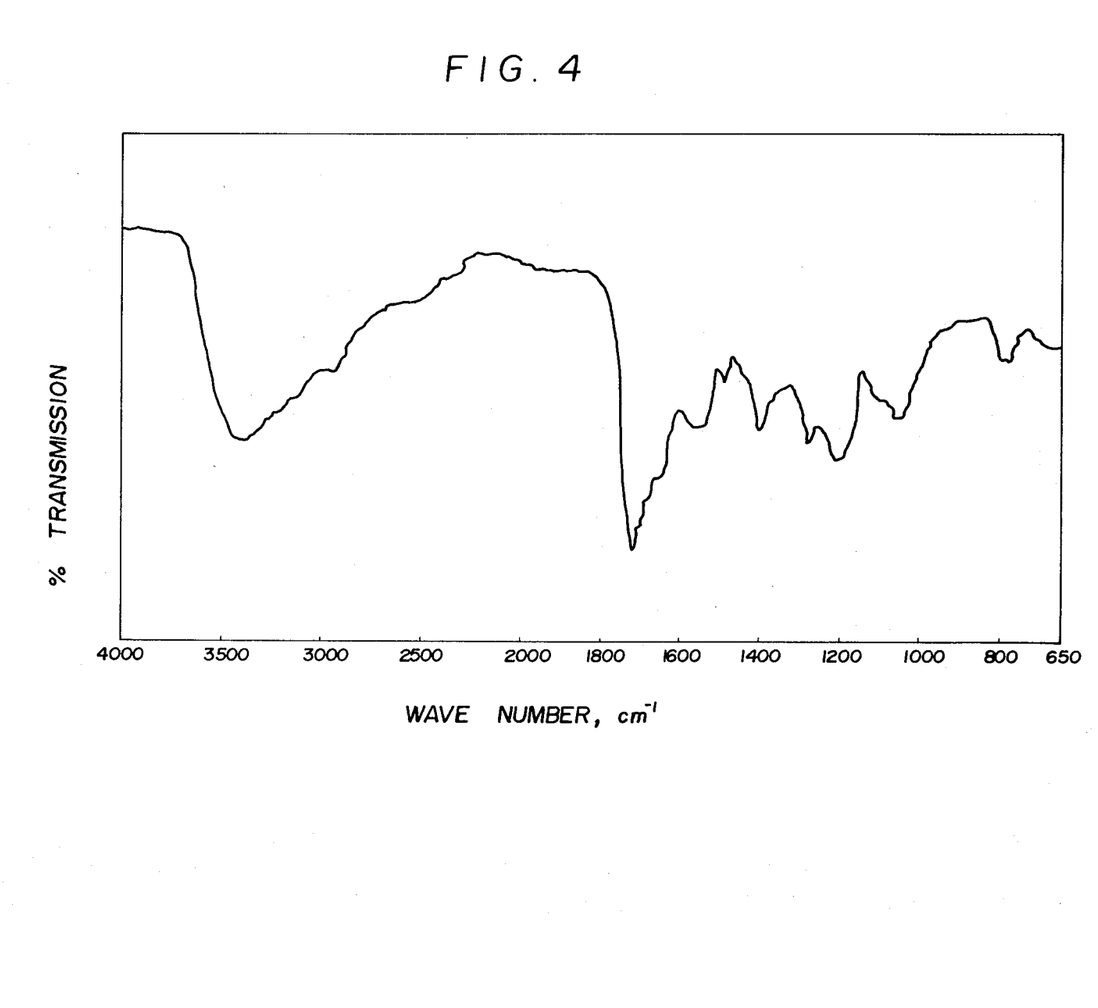
FIG. 4 illustrates an infrared absorption spectrum of the inventive polymer of which the pendant group on the DIVEMA backbone structure is 1-β-D-arabinofuranosylcytosine.

This powdery product contained 37.6% by weight of AraC according to the estimation from the absorption spectrum in the ultraviolet region. The absorption band in the ultraviolet region had a maximum at 271.5 nm. FIG. 4 shows the infrared absorption spectrum of this material in KBr tablet.

EXAMPLE 7

Substantially the same preparation procedure as in Example 6 was repeated using 500 mg of the same DIVEMA polymer, 40 ml of N-methylpyrrolidone, 250 mg of AraC and 0.25 ml of triethylamine to give 664 mg of the product which contained 19.1% by weight of AraC.

EXAMPLE 8

Figure 5:
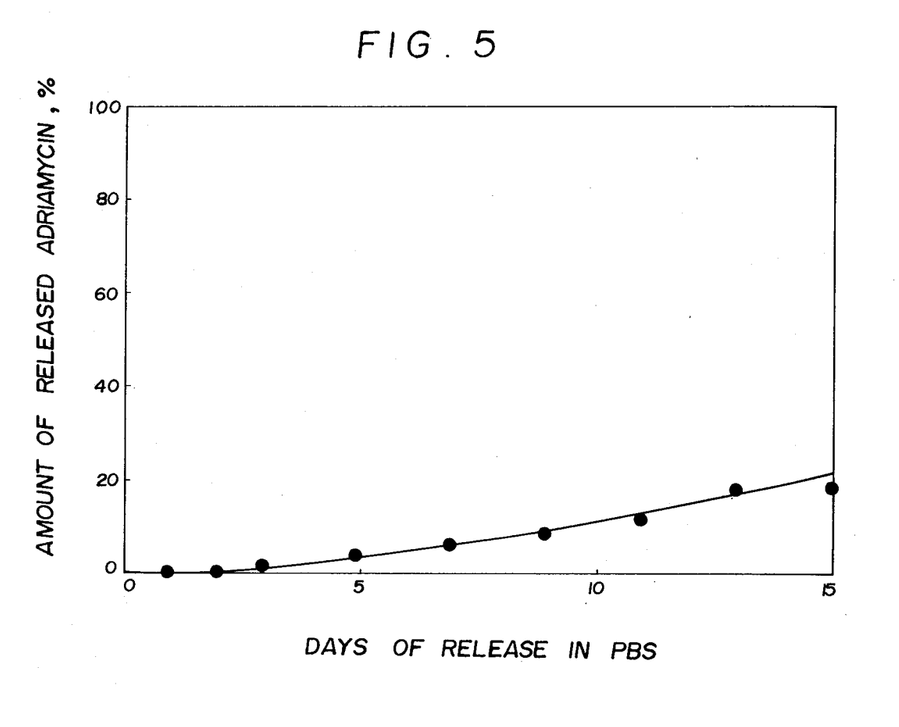
FIG. 5 is a graphic showing of the rate of in vitro release of adriamycin from an inventive polymeric compound having adriamycin pendant groups.

The rate of sustained release of adriamycin from the product polymer obtained in Example 1 was examined in a physiological saline solution (PBS) buffered with a 0.1N phosphate buffer solution at a pH of 7.2. Thus, 3.3 mg of the product obtained in Example 1 were dissolved in 10 ml of the PBS to be kept at 37° C. and a 0.1 μl portion of the solution was periodically taken and added to 0.4 ml of a 0.1N hydrochloric acid followed by centrifugal separation to remove the precipitates and determination of the absorbance of the supernatant liquid at a wave length of 490 nm to calculate the concentration of adriamycin therein. The results for the % release of adriamycin are shown graphically in FIG. 5 as a function of time in days, in which each plot was for an average of three determinations. It is understood from the results that adriamycin is released sustainedly under the above described conditions reaching about 20% after two weeks.

EXAMPLE 9

A similar test to Example 8 for the release rate of the AraC from the inventive polymeric compound was undertaken with the product obtained in Example 6. Thus, 1 mg of the product obtained in Example 6 was dissolved in 1 ml of an unbuffered physiological saline solution to be kept at 37° C. and a small portion of the solution taken periodically was analyzed by the high-performance liquid chromatography to determine the concentration of the freed AraC. The results are graphically shown in FIG. 6 as a function of time in days.

Figure 6:
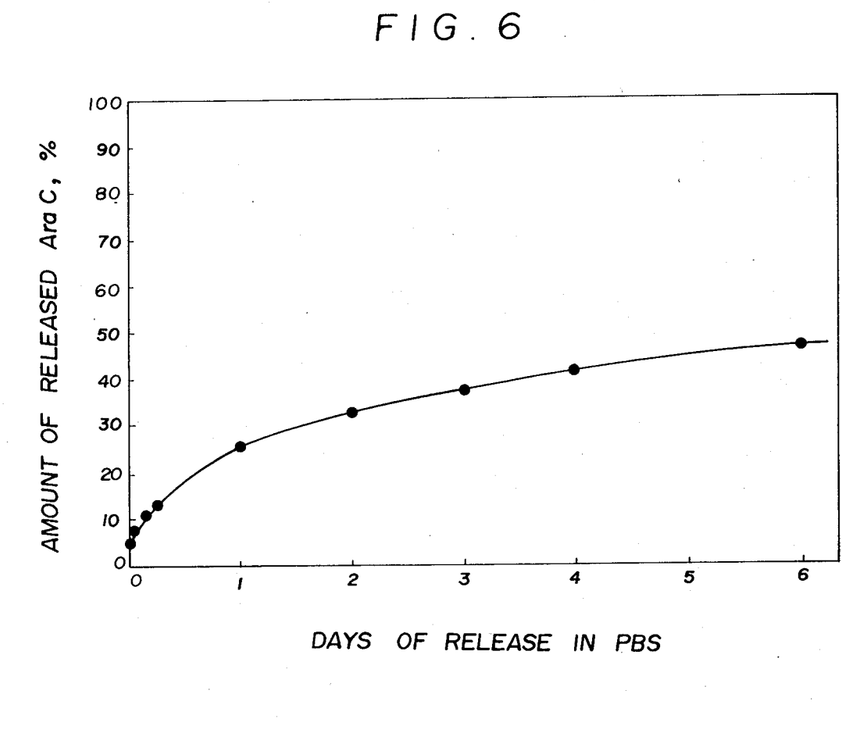
FIG. 6 is a graphic showing of the rate of in vitro release of 1-β-D-arabinofuranosylcytosine from the inventive polymeric compound having the same as the pendant groups.

As is understood from the results shown in this figure, AraC is gradually released from the polymer and the released amount is about 50% after one week under the above conditions.

EXAMPLE 10

Animal tests were undertaken to evaluate the antitumor effectiveness of the polymers in the salt form prepared in similar manners to the preceding Examples and containing 32.8% by weight of adriamycin and 30% by weight of daunomycin, respectively. These polymers are referred to as Ad-DIVEMA and Dau-DIVEMA, respectively, hereinbelow.

Thus, six a group of CDF$_1$ male mice of 8 to 10 weeks old intraperitoneally implanted with 1×10$^6$ P388 leukemia cells were once administrated 24 hours after the implantation with the aqueous solution of the Ad-DIVEMA or Dau-DIVEMA in the intraperitoneal cavity. The amount of administration is shown in Tables 1 and 2 for Ad-DIVEMA and Dau-DIVEMA, respectively, as calculated for the polymers and adriamycin or daunomycin contained therein. The life prolongation was calculated by comparing the median of the days of survival with that of the control group using the following equation:

$$\text{life prolongation ILS, \%} = (T-C)/C \times 100,$$

in which T is the median of the days of survival in the test group and C is the corresponding value in the control group. The results are shown in Tables 1 and 2 for the Ad-DIVEMA and Dau-DIVEMA, respectively. These tables also include the comparative results obtained by the administration of adriamycin or daunomycin, respectively, as such.

TABLE 1

| Anti-tumor agent | Dose, mg/kg As Ad-DIVEMA | As adriamycin | Median of survival, days | Life prolongation ILS, % |
|---|---|---|---|---|
| Ad-DIVEMA | 488 | 160 | 3.5 | −67.6 |
|  | 243 | 80 | 7.5 | −30.6 |
|  | 122 | 40 | 45.5 | 321.3 |
|  | 61 | 20 | 72.5 | 569.4 |
|  | 30 | 10 | 24.8 | 128.6 |
|  | 15 | 5 | 19.5 | 80.5 |
| Adriamycin | — | 15 | 7.8 | −27.8 |
|  | — | 10 | 15.8 | 46.3 |
|  | — | 5 | 20.0 | 85.2 |
|  | — | 2.5 | 19.8 | 83.3 |
|  | — | 1.25 | 19.0 | 75.9 |
| Control | — | — | 10.8 | 0.0 |

TABLE 2

| Anti-tumor agent | Dose, mg/kg As Dau-DIVEMA | As daunomycin | Median of survival, days | Life prolongation ILS, % |
|---|---|---|---|---|
| Dau-DIVEMA | 200 | 60 | 13.1 | 31 |
|  | 138 | 40 | 19.8 | 98 |
|  | 67 | 20 | 19.7 | 97 |
|  | 33 | 10 | 17.7 | 77 |
| Daunomycin | — | 8 | 14.8 | 48 |
| Control | — | — | 10.0 | 0 |

EXAMPLE 11

Similar animal tests to Example 10 were undertaken with three polymers prepared from the same DIVEMA polymer as used in Example 1 and containing 38%, 19% and 12%, respectively, by weight of AraC, referred to as AraC-DIVEMA hereinbelow, by intraperitoneally administrating the tumor cell-implanted mice with a physiological saline solution containing 1% by weight of sodium hydrogencarbonate and the AraC-DIVEMA in a calculated amount. The results of the life prolongation ILS are shown in Table 3 together with the comparative data obtained with administration of AraC as such. The table also includes the number of the mice in each group which could survive after 30 days from the implantation of the tumor cells.

TABLE 3

| Content of AraC, % by weight | Dose, mg/kg As AraC-DIVEMA | As AraC | Median of survival, days | Life prolongation ILS, % | Number of mice survived after 30 days |
|---|---|---|---|---|---|
| 38 | 213 | 80 | 3.5 | −65 | 1/6 |
|  | 106 | 40 | 26.5 | 165 | 1/6 |
|  | 53 | 20 | 21.3 | 113 | 0/6 |
|  | 27 | 10 | 19.8 | 98 | 0/6 |
| 19 | 419 | 80 | 7.8 | −28 | 0/6 |
|  | 209 | 40 | 18.8 | 88 | 0/6 |
|  | 105 | 20 | 18.1 | 81 | 0/6 |
|  | 52 | 10 | 17.3 | 73 | 0/6 |
| 12 | 672 | 80 | 5.9 | −41 | 0/6 |
|  | 336 | 40 | 20.6 | 106 | 0/6 |
|  | 168 | 20 | 16.8 | 68 | 0/6 |
|  | 84 | 10 | 14.8 | 48 | 0/6 |
| AraC | — | 80 | 11.0 | 10 | 0/6 |
| Control | — | — | 10.0 | 0 | 0/9 |

What is claimed is:

1. A polymeric compound having a polymeric backbone structure which is a copolymeric moiety of maleic anhydride and divinyl ether and at least one pendant moiety thereon selected from the class consisting of adriamycin, daunomycin and 1-β-D-arabinofuranosylcytosine bonded to the backbone structure through an amide linkage at the maleic anhydride unit thereof with the maleic anhydride units converted to carboxyl acid form comprising a unit represented by the structural formula in which n is a positive integer and R is the pendant moiety expressed by the formula R' being a hydroxyl group or a methyl group, or the formula or a pharmacologically acceptable salt thereof.

2. The polymeric compound as claimed in claim 1 wherein the content of the pendant moiety is in the range from 5 to 40% by weight.

3. The polymeric compound as claimed in claim 1 wherein the copolymeric moiety of maleic anhydride and divinyl ether has a molecular weight of 100,000 or smaller.

4. The polymeric compound as claimed in claim 1 wherein the pharmacologically acceptable salt is a salt with a metal selected from the class consisting of sodium, potassium, calcium and magnesium.

5. A method for the preparation of a polymeric compound having a polymeric backbone structure which is a copolymeric moiety of maleic anhydride and divinyl ether and at least one pendant moiety thereon selected from the class consisting of adriamycin, daunomycin and 1-β-D-arabinofuranosylcytosine bonded to the backbone structure through an amide linkage at the maleic anhydride unit thereof with the maleic anhydride units converted to carboxyl acid form comprising a unit represented by the structural formula in which n is a positive integer and R is the pendant moiety expressed by the formula R' being a hydroxyl group or a methyl group, or the formula which comprises reacting a copolymer of maleic anhydride and divinyl ether with an amino group containing compound selected from the class consisting of adriamycin, daunomycin and 1-β-D-arabinofuranosylcytosine in an organic solvent in the presence of a catalyst and hydrolyzing the unreacted maleic anhydride units into the free acid form.

* * * * *